US008223326B2

(12) United States Patent
Kim et al.

(10) Patent No.: US 8,223,326 B2
(45) Date of Patent: Jul. 17, 2012

(54) DARK-FIELD EXAMINATION DEVICE

(75) Inventors: Tai-Wook Kim, Seoul (KR); Heui-Jae Park, Seoul (KR); Il-Hwan Lee, Seoul (KR)

(73) Assignee: Snu Precision Co., Ltd., Seoul (KR)

( * ) Notice: Subject to any disclaimer, the term of this patent is extended or adjusted under 35 U.S.C. 154(b) by 30 days.

(21) Appl. No.: 12/673,525

(22) PCT Filed: Jan. 16, 2009

(86) PCT No.: PCT/KR2009/000249
§ 371 (c)(1),
(2), (4) Date: Feb. 15, 2010

(87) PCT Pub. No.: WO2009/104871
PCT Pub. Date: Aug. 27, 2009

(65) Prior Publication Data
US 2011/0043794 A1    Feb. 24, 2011

(30) Foreign Application Priority Data

Feb. 19, 2008 (KR) .................. 10-2008-0014859

(51) Int. Cl.
*G01N 21/00* (2006.01)

(52) U.S. Cl. .............. 356/237.1; 356/237.4; 250/559.28

(58) Field of Classification Search .... 356/237.1–237.5, 356/601–604; 250/237 G
See application file for complete search history.

(56) References Cited

U.S. PATENT DOCUMENTS

| 4,207,467 A | * | 6/1980 | Doyle | ........................ 250/338.1 |
| 4,748,329 A | * | 5/1988 | Cielo et al. | ................ 250/559.28 |
| 4,907,888 A | * | 3/1990 | Clarke et al. | ................... 356/613 |
| 4,970,388 A | * | 11/1990 | Nishimura et al. | ....... 250/237 G |

(Continued)

FOREIGN PATENT DOCUMENTS

CN    2812292 Y    8/2006

(Continued)

OTHER PUBLICATIONS

Search Report for PCT/KR2009/000249 dated Aug. 28, 2009, 4 pages.

*Primary Examiner* — Sang Nguyen
(74) *Attorney, Agent, or Firm* — Dority & Manning, P.A.

(57) ABSTRACT

The present invention relates to a dark-field examination device. The dark-field examination device according to the present invention is characterized in that it comprises: an illumination unit for irradiating light towards an examination object on a base; a reflection unit for reflecting, back towards the examination object, incident light which has been reflected by means of the examination object or incident light which has passed through the base; and an imaging unit for imaging the examination object by receiving light which has been scattered by means of the examination object, and in that the illumination unit, the reflection unit and the imaging unit are arranged in such a way that part of the light which has been irradiated from the illumination unit is scattered by means of the examination object and falls incident upon the imaging unit while another part of the light which has been irradiated from the illumination unit falls incident upon the reflection unit, and the light reflected back towards the examination object by means of the reflection unit is scattered by means of the examination object and falls incident upon the imaging unit.

5 Claims, 5 Drawing Sheets

U.S. PATENT DOCUMENTS

| | | | | |
|---|---|---|---|---|
| 4,975,571 A | * | 12/1990 | McMurtry et al. | 250/231.16 |
| 5,333,048 A | * | 7/1994 | Michel et al. | 356/494 |
| 5,610,392 A | * | 3/1997 | Nagayama et al. | 250/226 |
| 6,256,097 B1 | * | 7/2001 | Wagner | 356/369 |
| 6,457,801 B1 | * | 10/2002 | Fish et al. | 347/19 |
| 6,801,358 B2 | * | 10/2004 | Shafer et al. | 359/355 |
| 7,489,399 B1 | * | 2/2009 | Lee | 356/369 |
| 2006/0092276 A1 | | 5/2006 | Ariglio et al. | |

FOREIGN PATENT DOCUMENTS

| | | |
|---|---|---|
| CN | 101049022 A | 10/2007 |
| JP | 6341958 A | 12/1994 |
| JP | 2008051666 A | 3/2008 |
| JP | 2008107132 A | 5/2008 |
| KR | 20030081579 A | 10/2003 |
| KR | 20070084560 A | 8/2007 |

* cited by examiner

DARK-FIELD EXAMINATION DEVICE

TECHNICAL FIELD

The present invention relates to a dark-field inspection apparatus, and more particularly to a dark-field inspection apparatus, in which light emitted from an illuminating unit and scattered or reflected to the outside of an image sensing unit that senses an image of a subject without entering the image sensing unit is recovered and reused in sensing the image of the subject.

BACKGROUND ART

In a manufacturing process of a semiconductor wafer and a flat panel display such as a liquid crystal display (LCD), a plasma display panel (PDP) and an organic light emitting diode (OLED), there is need of inspecting whether a unit process is successfully performed or not every time when each process is finished.

For example, a method for inspecting a defect such as a foreign material, a protruding part or a recessed part on a substrate, a method for inspecting a pattern on the substrate besides the defect, etc. are widely used in an LCD manufacturing process. As one of the methods for inspecting the defect or the pattern on the substrate, there is a dark field inspection method. Here, a subject to be inspected includes an object to be directly inspected, i.e., the foreign material or the pattern, and a base like a mirror.

FIG. 1 is a schematic view of a conventional dark-field inspection apparatus.

Referring to FIG. 1 the dark-field inspection apparatus is an apparatus for inspecting a subject 2 on a base 1, for example, a foreign material laid on a glass substrate, or a protruding part or a recessed part formed on a glass substrate. An illuminating unit 10 is arranged to emit light a1, a2 toward the subject 2 on the base 1. The light a1, a2 emitted from the illuminating unit 10 is reflected or scattered by the subject 2 such as a protruding part or reflected by the base 1 such as a glass substrate. Some light all of the light reflected and scattered by the subject 2 enter an image sensing unit 20 placed above the base 1, and thus the image sensing unit 20 uses the incident light a11 to sense an image of the subject 2. The image sensed by the image sensing unit 20 is analyzed in an image processing unit 30, so that it is possible to determine whether the subject 2 exists on the base 1 or which kind of the defect the subject 2 belongs to.

While some of the light a1, a2 emitted from the illuminating unit 10 are reflected and scattered by the subject 2 and travel toward the image sensing unit 20 (refer to a11), another some are reflected and scattered by the subject 2 and travel not to the image sensing unit 20 (refer to a12) or likewise reflected by the base 1 and travel not to the image sensing snit 20 (refer to a22). Thus, the light a12, a22 traveling not to the image sensing unit 20 wastes, so that a capacity light of the illuminating unit 10 is not fully used for sensing the image of the subject 2. Further, since the illuminating unit 10 emits the light in a certain direction, there arises a problem in that only a certain surface of the subject 2 is highlighted when sensing an image.

DISCLOSURE

Technical Problem

The present invention is conceived to solve the problems of the conventional techniques as described above, and an aspect of the present invention is to provide a dark-field inspection apparatus in which light that does not enter an image sensing unit for sensing an image of a subject but wastes is recovered and reused, so that light from an illuminating unit capable of emitting a certain light quantity can be optimally used to thereby enhance the performance and the efficiency thereof when observing and inspecting a substrate, and the recovered light is used at an opposite side so that many sides of the subject can be inspected without an additional illuminating unit.

Technical Solution

The foregoing and/or other aspects of the present invention are achieved by providing a dark-field inspection apparatus including: an illuminating unit which emits light toward a subject on a base; a reflecting unit which returns incident light reflected from the subject or incident light passed through the base toward the subject; and an image sensing unit which receives light scattered by the subject and senses an image of the subject, wherein the illuminating unit, the reflecting unit and the image sensing unit are arranged so that some of the light emitted from the illuminating unit can be scattered by the subject and incident on the image sensing unit, another some of the light emitted from the illuminating unit can be incident on the reflecting unit, and the light returned toward the subject again by the reflecting unit can be scattered by the subject and enters the image sensing unit.

The subject may be laid on one surface of the base, the illuminating unit and the reflecting unit may be arranged at a distance from the one surface of the base, and the light incident on the reflecting unit may include light reflected from the subject or light reflected from the base.

The illuminating unit and the reflecting unit may be arranged so that an optical axis connecting a center of the illuminating unit and a center of the reflecting unit can be substantially parallel with respect to the base.

The reflecting unit may include a first reflecting mirror to reflect the incident light reflected from the subject or the base, and a second reflecting mirror to reflect the incident light reflected from the first reflecting mirror again toward the subject, and an optical path between the subject and the first reflecting mirror may not coincide with an optical path between the second reflecting mirror and the subject.

The subject may be laid on one surface of the base, the illuminating unit may be arranged at a distance from the other surface opposite to the one surface of the base, and the reflecting unit may be arranged at a distance from the one surface of the base, and the light incident on the reflecting unit may include light reflected from the subject or light passed through the base.

The illuminating unit may include one of a laser, a light emitting diode (LED) and a halogen lamp.

The dark-field inspection apparatus may further include a condensing unit arranged in front of the reflecting unit with regard to an incident direction toward the reflecting unit, and condensing the light incident on or reflected from the reflecting unit.

Advantageous Effects

An exemplary embodiment of the present invention provides a dark-field inspection apparatus with a reflecting unit which can recover light that does not enter an image sensing unit for sensing an image of a subject but is scattered and reflected to the outside, and thus the light recovered by the reflecting unit is reused by entering the image sensing unit again, so that a set certain light quantity of the illuminating unit can be fully used without an additional illuminating unit.

Another exemplary embodiment of the present invention provides a dark-field inspection apparatus, in which an image of a subject can be sensed using light scattered from all parts of the subject, e.g. not only a part illuminated by the illuminating unit but also a part illuminated by the reflecting unit or the like part, so that the performance and the efficiency of inspecting the subject can be improved.

BEST MODE

Mode for Invention

Below, exemplary embodiments of a dark-field inspection apparatus according to the present invention will be described in more detail with reference to accompanying drawings.

Figure 2:
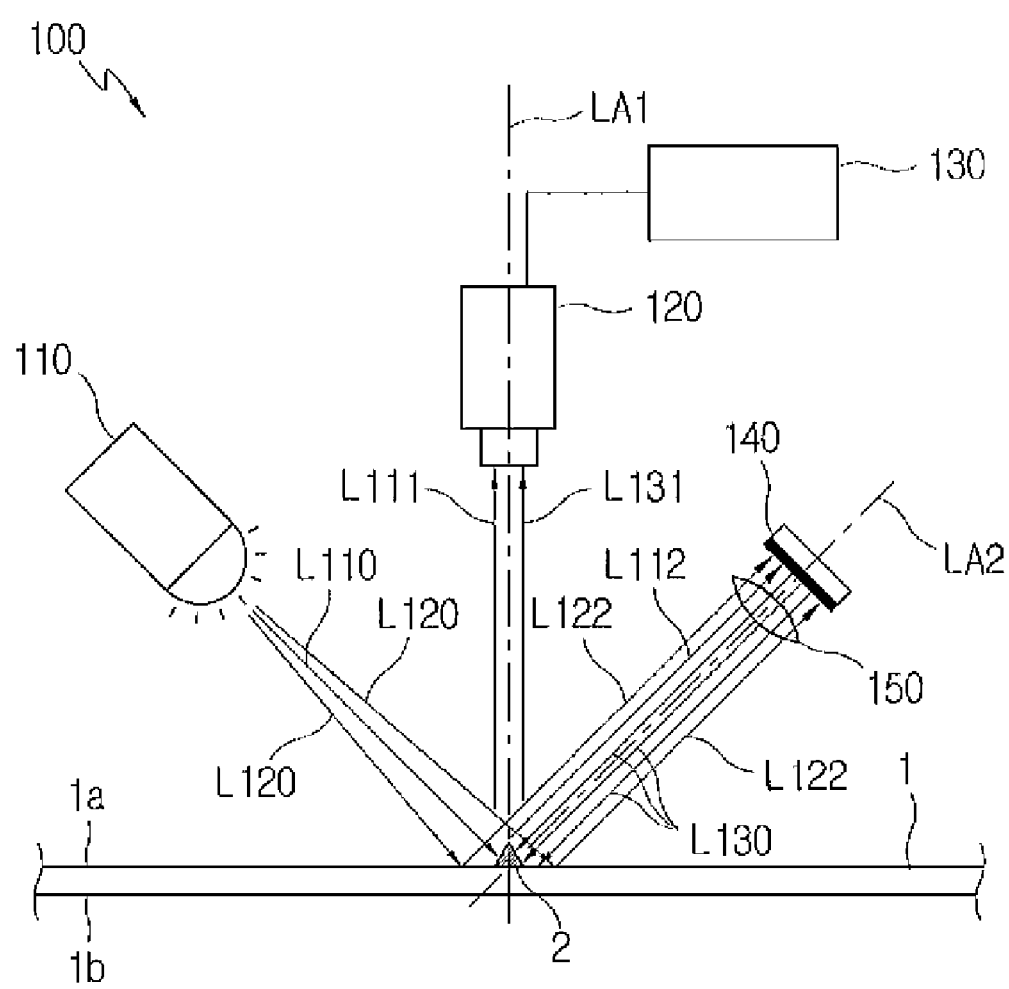
FIG. 2 is a schematic view of a dark-field inspection apparatus according to a first exemplary embodiment of the present invention.

FIG. 2 is a schematic view of a dark-field inspection apparatus according to a first exemplary embodiment of the present invention.

Referring to FIG. 2, the dark-field inspection apparatus 100 in this embodiment, which recovers light emitted from an illuminating unit and scattered or reflected to the outside of an image sensing unit that senses an image of a subject without entering the image sensing unit and reuses it in sensing the image of the subject, includes an illuminating unit 110, an image sensing unit 120, an image processing unit 130, a reflecting unit 140, and a condensing unit 150.

The illuminating unit 110 emits light toward a subject 2 on a base 1. The base 1 includes a glass substrate or the like employed in a flat panel display, and the subject 2 includes a foreign material laid on the glass substrate, and a protruding part or a recessed part formed on the glass substrate. As a light source for the light emitted from the illuminating unit 110, a laser, a light emitting diode (LED), or etc. can be generally used. Besides, various light sources can be employed.

The image sensing unit 120 condenses the light scattered by the subject 2 and senses the image of the subject 2. Here, a line camera, an area camera or etc. can be generally used as the image sensing unit 120. Besides, various image capturing means for the dark-field inspection apparatus can be used here. The light to be condensed by the image sensing unit 120 includes light L110, L111 emitted from the illuminating unit 110, scattered by the subject 2 and traveling toward the image sensing unit 120 along a first path LA1; and light L130, L131 reflected by the reflecting unit 140 to be described later, traveling toward the subject 2 along a second path LA2, scattered by the subject 2 and traveling toward the image sensing unit 120 along the first path LA1.

The image processing unit 130 analyzes the image of the subject 2, which is sensed by the image sensing unit 120, and determines whether the subject 2 is allowable or not with regard to an defectiveness inspection or which kind of defect the subject 2 belongs to.

The reflecting unit 140 reflects incident light, which is reflected by the subject 2 or passed through the base 1, toward the subject 2. Here, a mirror or the like, which is processed to reflect more than 99% of the incident light, is generally used as the reflecting unit 140. Besides, mirrors with various reflectivity may be used as the reflecting unit 140. The light incident on the reflecting unit 140 includes light L110, L112 emitted from the illuminating unit 110, reflected by the subject 2 and traveling toward the reflecting unit 140 along the second path LA2; and light L120, L122 emitted from the illuminating unit 110, reflected by the base 1 and traveling toward the reflecting unit 140 along the second path LA2.

The condensing unit 150, which condenses the light incident on or reflected from the reflecting unit 140, is arranged in front of the reflecting unit 140 along the second path LA2 with regard to an incident direction toward the reflecting unit 140. Here, a condenser lens or the like, used for condensing the light in a desired direction or place, is generally used as the condensing unit 150. The light that enters the reflecting unit 140 through the condensing unit 150 may be condensed on the surface of the reflecting unit 140, and the light that exits from the reflecting unit 140 may also be condensed in the vicinity of the subject 2. Further, a structure for controlling and using polarization of the reflected light may be added, in which the polarization of the reflected light is based on Brewster's law.

The dark-field inspection apparatus according to this embodiment is characterized in that the illuminating unit 110 and the reflecting unit 140 are arranged on the same side with respect to the base 1. The subject 2 is laid on one surface 1a of the base 1, and the illuminating unit 110 and the reflecting unit 140 are arranged at a distance from the one surface 1a of the base 1. Thus, some of the light emitted from the illuminating unit 110 are reflected from the subject 2 and incident on the reflecting unit 140 (see L110, L112), but another some of the light emitted from the illuminating unit 110 is reflected from the base 1 and incident on the reflecting unit 140 (see L120, L122)

Below, the traveling path of the light emitted from the illuminating unit 110 in the dark-field inspection apparatus with the foregoing configuration according to this embodiment will be schematically described with reference to FIG. 2.

Some of the light emitted from the illuminating unit 110 are scattered by the subject 2 and travel toward the image sensing unit 120 along the first path LA1 (see L110, L111). Another some of the light emitted from the illuminating unit 110 are reflected from the subject 2 and incident on the reflecting unit 140 along the second path LA2 (see L110, L112). Still another some of the light emitted from the illuminating unit 110 are reflected by the base 1 and incident on the reflecting unit 140 along the second path LA2 (see L120, L122).

Thus, the light L112, L122 incident on the reflecting unit 140 via the condensing unit 150 is reflected and travels toward the subject 2. The light L130 reflected by the reflecting unit 140 travels toward the subject 2 along the second path LA2, and is scattered again by the subject 2 to thereby travel toward the image sensing unit 120 along the first path LA1 (see L131).

The dark-field inspection apparatus with the foregoing configuration according to this embodiment is provided with the reflecting unit which can recover the light that does not enter the image sensing unit for sensing the image of the subject but is scattered and reflected to the outside, and thus the light recovered by the reflecting unit is reused by entering the image sensing unit again, so that a set certain light quantity of the illuminating unit can be fully used without an additional illuminating unit.

Further, the image of the subject can be sensed using the light scattered from all parts of the subject, e.g. not only a part illuminated by the illuminating unit but also a part illuminated by the reflecting unit or the like part, so that the performance and the efficiency of inspecting the subject can be improved.

Figure 3:
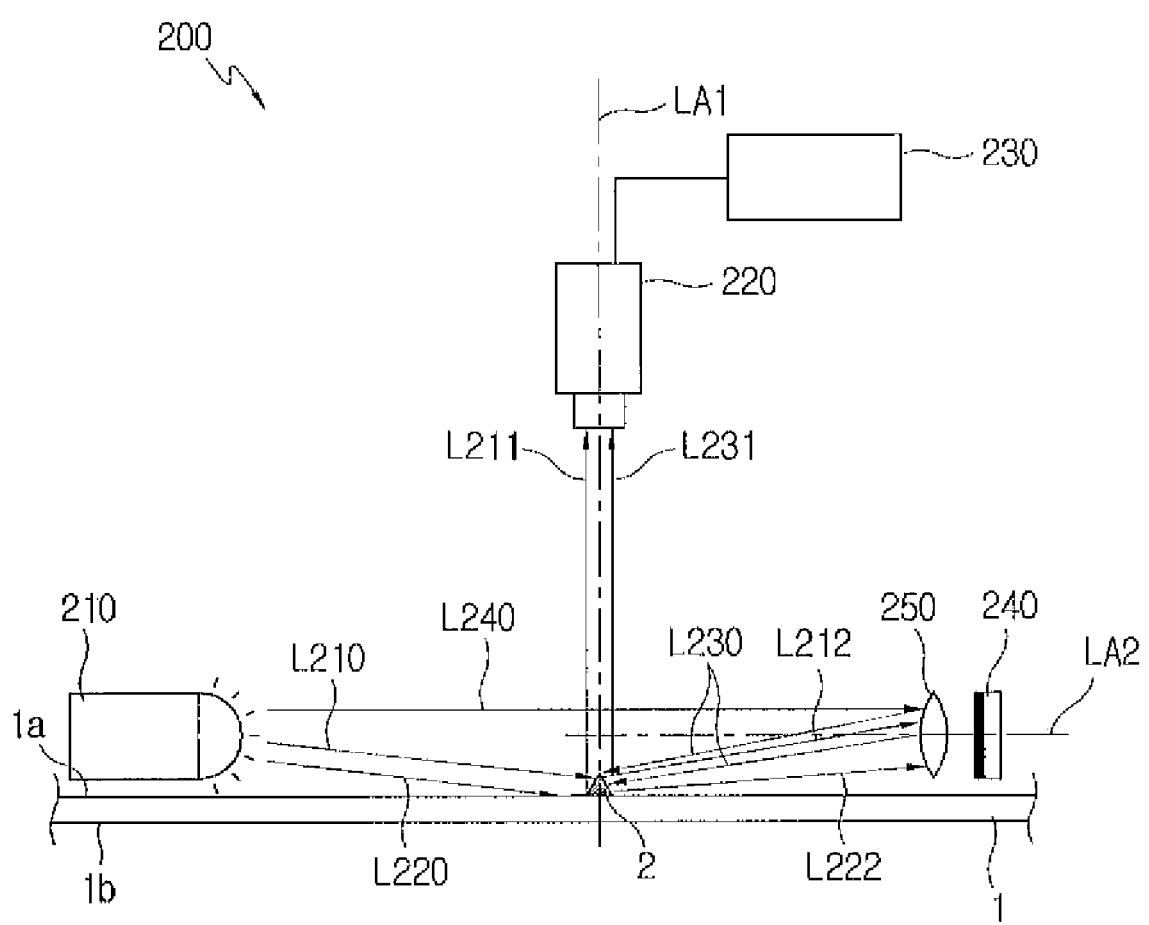
FIG. 3 is a schematic view of a dark-field inspection apparatus according to a second exemplary embodiment of the preset invention.

Meanwhile, FIG. 3 is a schematic view of a dark-field inspection apparatus according to a second exemplary embodiment of the present invention.

Figure 1:
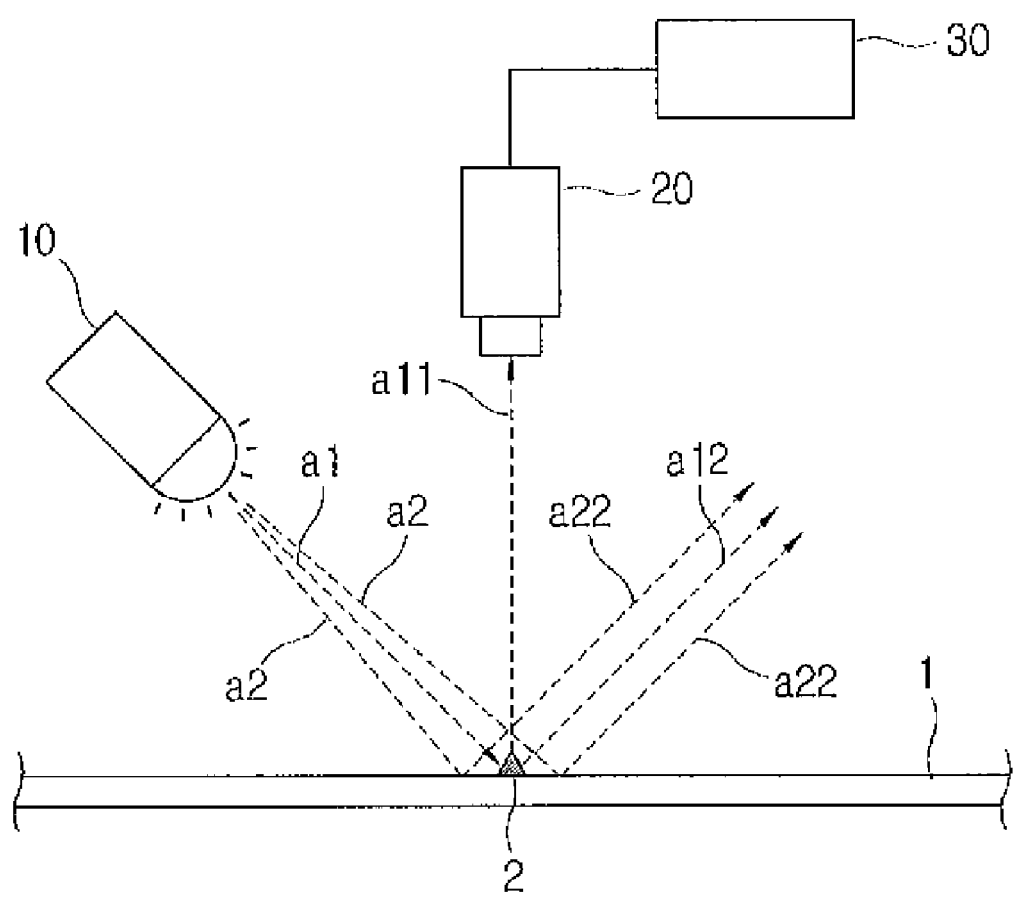
FIG. 1 is an exemplary schematic view of a conventional dark-field inspection apparatus.

Referring to FIG. 3, the dark-field inspection apparatus 200 in this embodiment, which recovers light emitted from an illuminating unit and scattered or reflected to the outside of an image sensing unit that senses an image of a subject without entering the image sensing unit and reuses it in sensing the image of the subject, includes an illuminating unit 210, an image sensing unit 220, an image processing unit 230, a reflecting unit 240, and a condensing unit 250. For reference, the illuminating unit 210, the image sensing unit 220, the image processing unit 230, the reflecting unit 240 and the condensing unit 250 of FIG. 3 have the same configurations and functions as the illuminating unit 110, the image sensing unit 120, the image processing unit 130, the reflecting unit 140 and the condensing unit 150 of FIG. 1, and therefore detailed descriptions thereof will be avoided as necessary.

The dark-field inspection apparatus 200 according to this embodiment is characterized in that the illuminating unit 210 and the reflecting unit 240 are arranged on the same side with respect to the base 1, and arranged so that an optical axis connecting the center of the illuminating unit 210 and the center of the reflecting unit 240 can be substantially parallel (parallel or inclined at a little angle) with respect to the base 1. The optical axis passing through the center of the image sensing unit 220 is perpendicular to the base 1, and at the same time perpendicular to the optical axis passing through the illuminating unit 210 and the center of the reflecting unit 240.

Thus, some of the light emitted from the illuminating unit 210 are directly incident on the reflecting unit 240 without any interference due to a medium (see L240), another some of the light emitted from the illuminating unit 210 are reflected from the subject 2 and incident on the reflecting unit 240 (see L210, L212), and still another some of the light emitted from the illuminating unit 210 are reflected from the base 1 and incident on the reflecting unit 240 (see L220, L222).

Some of the light emitted from the illuminating unit 210 is scattered by the subject 2 and travel toward the image sensing unit 220 along the first path LA1 (see L210, L211), and the light (L230) reflected from the reflecting unit 240 travels toward the subject 2 along the second path LA2, is scattered by the subject 2 again and travels toward the image sensing unit 220 along the first path LA1 (see L231).

Figure 4:
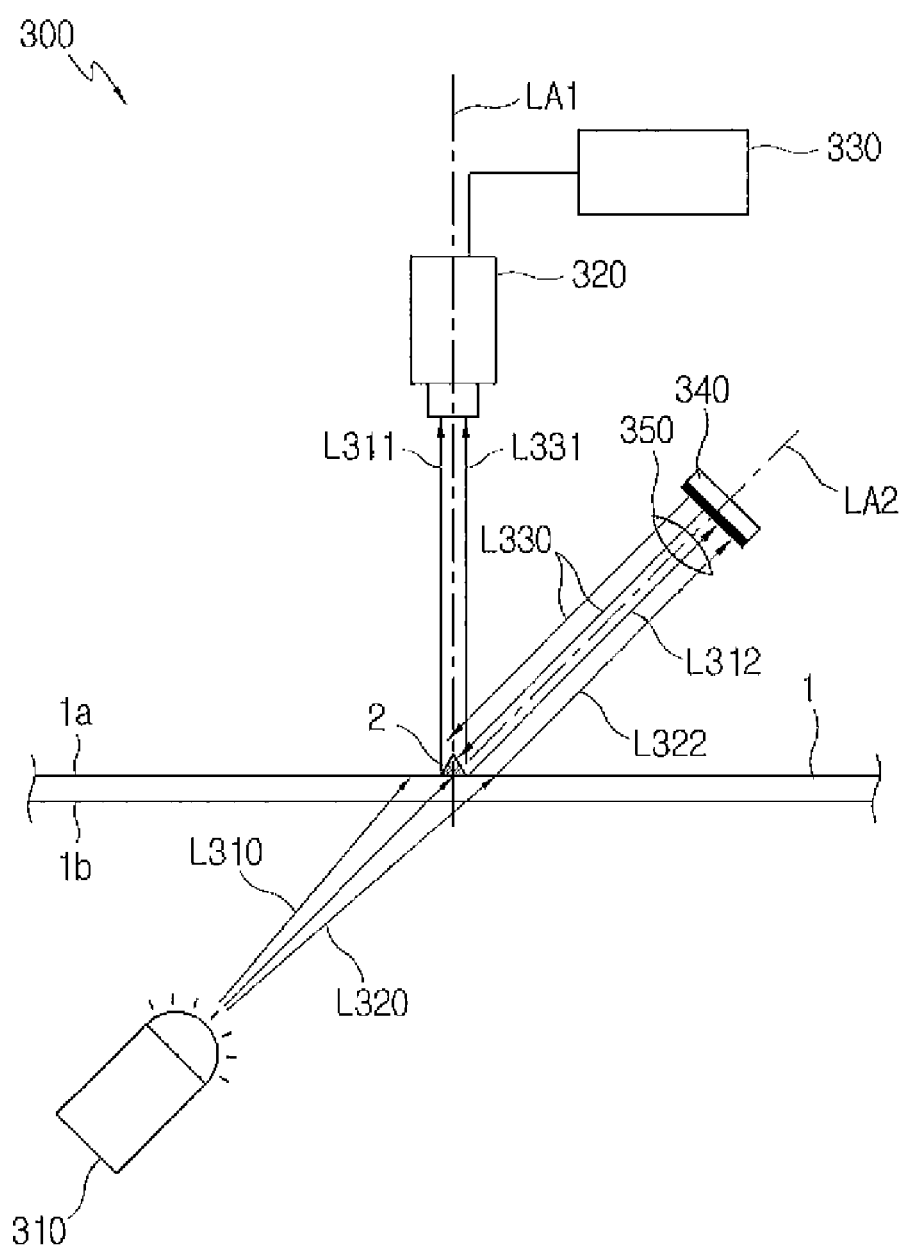
FIG. 4 is a schematic view of a dark-field inspection apparatus according to a third exemplary embodiment of the present invention.

In the meantime, FIG. 4 is a schematic view of a dark-field inspection apparatus according to a third exemplary embodiment of the present invention.

Referring to FIG. 4, the dark-field inspection apparatus 300 in this embodiment, which recovers light emitted from an illuminating unit and scattered or reflected to the outside of an image sensing unit that senses an image of a subject without entering the image sensing unit and reuses it in sensing the image of the subject, includes an illuminating unit 310, an image sensing unit 320, an image processing unit 330, a reflecting unit 340, and a condensing unit 350. For reference, the illuminating unit 310, the image sensing unit 320, the image processing unit 330, the reflecting unit 340 and the condensing unit 350 of FIG. 4 have the same configurations and functions as the illuminating unit 110, the image sensing unit 120, the image processing unit 130, the reflecting unit 140 and the condensing unit 150 of FIG. 1, and therefore detailed descriptions thereof will be avoided as necessary.

The dark-field inspection apparatus 300 according to this embodiment is characterized in that the illuminating unit 310 and the reflecting unit 340 are arranged on different sides, respectively, with respect to the base 1. The subject 2 is laid on one surface 1a of the base 1, and the illuminating unit 310 is arranged at a distance from the other surface 1b opposite to the one surface 1a of the base 1. Further, the reflecting unit 340 is arranged at a distance from the one surface 1a of the base 1.

Thus, some of the light emitted from the illuminating unit 310 are passed through the base 1, scattered by the subject 2 and incident on the image sensing unit 320 (refer to L310, L311). Another some of the light emitted from the illuminating unit 310 are passed through the base 1, reflected from the subject 2 and incident on the reflecting unit 340 (refer to L310, L312). Still another some of the light emitted from the illuminating unit 310 are passed through the base 1 and incident on the reflecting unit 340. The light (L330) reflected from the reflecting unit 340 travels toward the subject 2 along the second path LA2, is scattered by the subject 2 again and travels toward the image sensing unit 320 along the first path LA1 (see L331).

Figure 5:
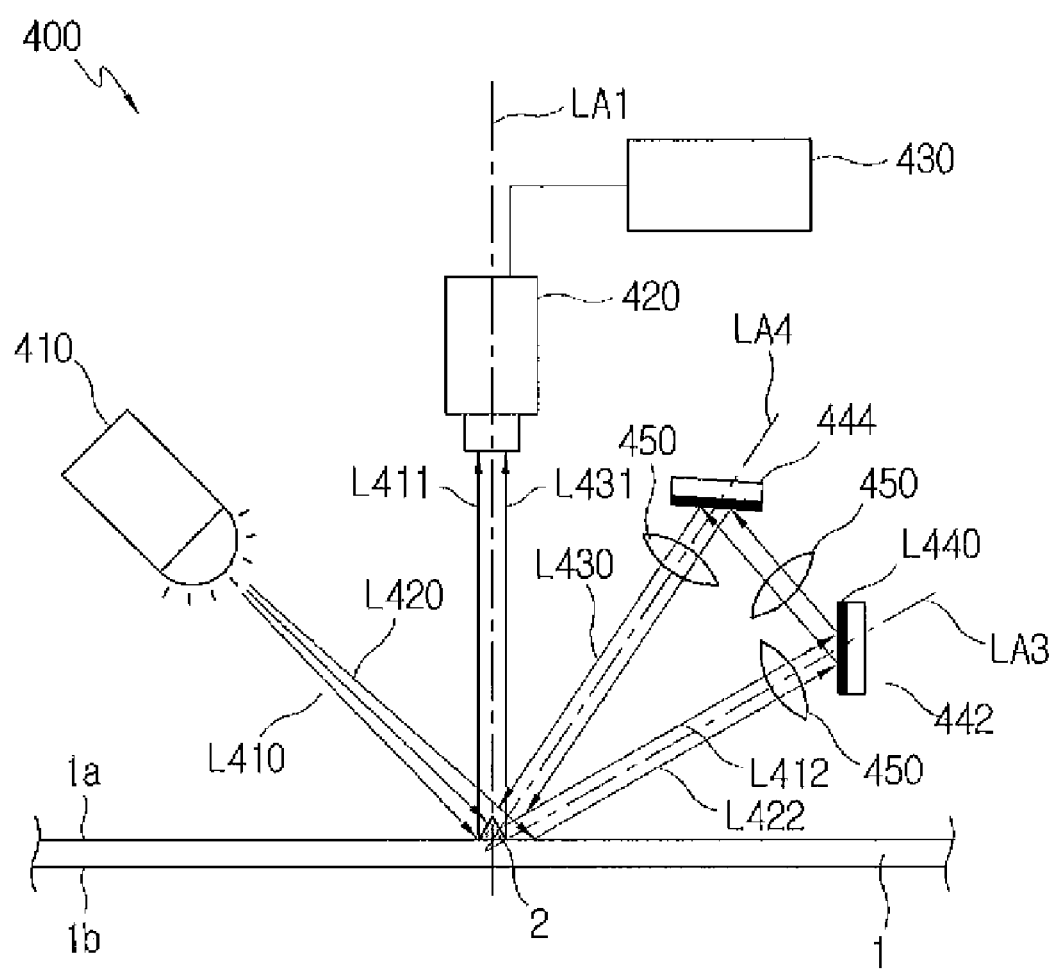
FIG. 5 is a schematic view of a dark-field inspection apparatus according to a fourth exemplary embodiment of the present invention.

In the meantime, FIG. 5 is a schematic view of a dark-field inspection apparatus according to a fourth exemplary embodiment of the present invention.

Referring to FIG. 5, the dark-field inspection apparatus 400 in this embodiment, which recovers light emitted from an illuminating unit and scattered or reflected to the outside of an image sensing unit that senses an image of a subject without entering the image sensing unit and reuses it in sensing the image of the subject, includes an illuminating unit 410, an image sensing unit 420, an image processing unit 430, a reflecting unit 442, 444, and a condensing unit 450. For reference, the illuminating unit 410, the image sensing unit 420, the image processing unit 420, the reflecting unit 442, 444 and the condensing unit 450 of FIG. 5 have the same configurations and functions as the illuminating unit 110, the image sensing unit 120, the image processing unit 130, the reflecting unit 140 and the condensing unit 150 of FIG. 1, and therefore detailed descriptions thereof will be avoided as necessary.

The dark-field inspection apparatus 400 according to this embodiment is characterized in that the reflecting unit includes a first reflecting mirror 442 reflecting incident light reflected from the subject 2 or the base 1, and a second reflecting mirror 444 reflecting incident light reflected from the first reflecting mirror 442 toward the subject 2 again. The subject 2 is laid on one surface 1a of the base 1, and the illuminating unit 410, the first reflecting mirror 442 and the second reflecting mirror 444 are arranged at a difference from the one surface 1a of the base 1.

Thus, some of the light emitted from the illuminating unit 410 are scattered by the subject 2 and travel toward the image sensing unit 420 along the first path LA1 (see L410, L411), another some of light emitted from the illuminating unit 410 are reflected from the subject 2 and incident on the first reflecting mirror 442 along a third path LA3 (see L410, L412), and still another some of the light emitted from the illuminating unit 410 are reflected from the base 1 and incident on the first reflecting mirror 442 (see L420, L422).

The light incident on the first reflecting mirror 442 is totally reflected from the first reflecting mirror 442 and travels toward the second reflecting mirror 444 (see L440), and the light incident on the second reflecting mirror 444 is reflected from the second reflecting mirror 444 and travels toward the subject 2 again along a fourth path LA4 (see L430). The light traveling toward the subject 2 is scattered by the subject 2 and then travels toward the image sensing unit 420 along the first path LA1 (see L431).

In this embodiment, the first reflecting mirror 442 and the second reflecting mirror 444 are arranged so that an optical path between the subject 2 and the first reflecting mirror 442 cannot be coincident with an optical path between the second reflecting mirror 444 and the subject 2. Further, an optical device such as the condensing unit 450 (e.g., condenser lens), a polarization plate or the like may be added on the optical path between the subject 2 and the first reflecting mirror 442. Likewise, an optical device such as a condenser lens, a polarization plate or the like may be added on an optical path between the first reflecting mirror 442 and the second reflecting mirror 444 or the optical path between the second reflecting mirror 444 and the subject 2.

The dark-field inspection apparatus with the foregoing configuration according to this embodiment is provided with the pair of reflecting units so that there is no need of making the optical path for being incent on the reflecting unit coincide with the optical path of being reflected from the reflecting unit. Accordingly, it is possible to apply various configurations to the apparatus and have an effect on enhancing compatibility to correspond to various cases.

Although the present invention has been described with reference to the embodiments and the accompanying drawings, it will be apparent to those skilled in the art that the embodiments are given by way of illustration, and that various modifications and equivalent embodiments can be made without departing from the spirit and scope of the present invention. Accordingly, the scope of the present invention should be limited only by the accompanying claims.

INDUSTRIAL APPLICABILITY

The present invention can be used in a dark-field inspection apparatus which recovers light emitted from an illuminating unit and scattered or reflected to the outside of an image sensing unit that senses an image of a subject without entering the image sensing unit and reuses it in sensing the image of the subject.

The invention claimed is:

1. A dark-field inspection apparatus comprising:
an illuminating unit which emits light toward a region where a subject on a base is positioned;
a reflecting unit which returns incident light reflected from the subject or incident light passed through the base toward the subject, wherein the reflecting unit comprises a first reflecting mirror to reflect the incident light reflected from the subject or the base, and a second reflecting mirror to reflect the incident light reflected from the first reflecting mirror again toward the subject, and wherein an optical path exists between the subject and the first reflecting mirror without coinciding with an optical path between the second reflecting mirror and the subject; and
an image sensing unit which receives light scattered by the subject and senses an image of the subject,
wherein the subject is laid on one surface of the base, and the illuminating unit and the reflecting unit are arranged at a distance from the one surface of the base, and the light incident on the reflecting unit comprises light reflected from the subject or light reflected from the base, and
wherein the illuminating unit, the reflecting unit and the image sensing unit are arranged so that some of the light emitted from the illuminating unit is scattered by the subject and enters the image sensing unit, and some of the light emitted from the illuminating unit is returned toward the subject by the reflecting unit, is scattered by the subject and then enters the image sensing unit to improve efficiency of using light.

2. The dark-field inspection apparatus according to claim 1, wherein the illuminating unit and the reflecting unit are arranged so that an optical axis connecting a center of the illuminating unit and a center of the reflecting unit can be substantially parallel with the base.

3. The dark-field inspection apparatus according to claim 1, wherein the subject is laid on one surface of the base, the illuminating unit is arranged at a distance from the other surface opposite to the one surface of the base, and the reflecting unit is arranged at a distance from the one surface of the base, and
the light incident on the reflecting unit comprises light reflected from the subject or light passed through the base.

4. The dark-field inspection apparatus according to claim 1, wherein the illuminating unit comprises one of a laser, a light emitting diode (LED) and a halogen lamp.

5. The dark-field inspection apparatus according to claim 1, further comprising a condensing unit arranged in front of the reflecting unit with regard to an incident direction toward the reflecting unit, and condensing the light incident on or reflected from the reflecting unit.

* * * * *